United States Patent
Björling et al.

(10) Patent No.: US 7,979,125 B2
(45) Date of Patent: Jul. 12, 2011

(54) IMPLANTABLE BIVENTRICULAR HEART STIMULATING DEVICE AND METHOD FOR PERFORMING A CAPTURE THRESHOLD SEARCH

(75) Inventors: Anders Björling, Solna (SE); Nils Holmström, Järfälla (SE); Karin Järverud, Solna (SE)

(73) Assignee: St. Jude Medical AB, Jarfalla (SE)

( * ) Notice: Subject to any disclaimer, the term of this patent is extended or adjusted under 35 U.S.C. 154(b) by 549 days.

(21) Appl. No.: 12/090,157

(22) PCT Filed: Oct. 31, 2005

(86) PCT No.: PCT/SE2005/001629
§ 371 (c)(1),
(2), (4) Date: Sep. 17, 2008

(87) PCT Pub. No.: WO2007/053064
PCT Pub. Date: May 10, 2007

(65) Prior Publication Data
US 2009/0149908 A1 Jun. 11, 2009

(51) Int. Cl.
*A61N 1/362* (2006.01)
(52) U.S. Cl. .......................................... 607/28
(58) Field of Classification Search .................. None
See application file for complete search history.

(56) References Cited

U.S. PATENT DOCUMENTS

| | | | |
|---|---|---|---|
| 5,716,383 A | 2/1998 | Kieval et al. | |
| 5,720,768 A | 2/1998 | Verboven-Nelissen | |
| 6,122,545 A | 9/2000 | Struble et al. | |
| 6,456,881 B1 | 9/2002 | Bornzin et al. | |
| 6,498,950 B1 | 12/2002 | Bradley | |
| 6,832,112 B1 | 12/2004 | Bornzin | |
| 6,904,321 B1 | 6/2005 | Bornzin et al. | |
| 6,915,164 B2 * | 7/2005 | Bradley et al. | 607/29 |
| 7,228,172 B2 * | 6/2007 | Jarverud et al. | 607/9 |
| 2001/0049542 A1 * | 12/2001 | Florio et al. | 607/28 |
| 2003/0195579 A1 * | 10/2003 | Bradley et al. | 607/27 |

FOREIGN PATENT DOCUMENTS
EP 1 430 928 6/2004
WO WO 2005/028030 3/2005
* cited by examiner

*Primary Examiner* — Kennedy J Schaetzle
(74) *Attorney, Agent, or Firm* — Schiff Hardin LLP

(57) ABSTRACT

In an implantable biventricular heart stimulating device, and a biventricular heart stimulating method, wherein operation takes place normally with a time VV between a pacing pulse delivered, or inhibited, by a first ventricular pacing circuit and a pacing pulse delivered, or inhibited, by a second ventricular pacing circuit, and wherein a time $VV_{cts}$ is determined that is to be used instead of VV during a capture threshold search.

41 Claims, 3 Drawing Sheets

ID TABLE BIVENTRICULAR HEART STIMULATING DEVICE AND METHOD FOR PERFORMING A CAPTURE THRESHOLD SEARCH

BACKGROUND OF THE INVENTION

1. Field of the Invention

The present invention relates to an implantable heart stimulating device with which it is possible to stimulate both the ventricles of a heart, i.e. a bi-ventricular pacer.

The invention also relates to a system including such a device and to a method of, in a human or animal being, performing a capture threshold search.

2. Description of the Prior Art

Several different implantable devices for stimulating a heart are known. The devices are normally able to sense the electrical activity of the heart, Some implantable devices are able to deliver stimulation pulses to and/or sense the right atrium (in some case even the left atrium) and also to deliver stimulation pulses to and sense both the left and right ventricle.

Devices that are able to deliver stimulation pulses to both the left and right ventricle can be called bi-ventricular pacers. Such devices can be used to treat patients who suffer from different severe cardiac problems, e.g. patients suffering from congestive heart failure (CHF). CHF is defined generally as the inability of the heart to deliver a sufficient amount of blood to the body. CHF can have different causes. It can for example be caused by a left bundle branch block (LBBB) or a right bundle branch block (RBBB). By using bi-ventricular pacing, the contraction of the ventricles can be controlled in order to improve the ability of the heart to pump blood. The stimulation pulses to the two ventricles can be delivered simultaneously but it is also known that the stimulation pulses to the two ventricles are delivered with a short time delay between them in order to optimize the pumping performance of the heart.

U.S. Pat. No. 5,720,768 describes different possible electrode positions in order to stimulate or sense the different chambers of the heart.

U.S. Pat. No. 6,070,100 describes that electrodes may be positioned in both the left and the right atrium as well as in the left and the right ventricles.

In connection with implantable pacers, it is known to detect the capture of the heart, i.e. to detect whether the heart actually reacts to a delivered stimulation pulse. If the heart is not captured, it is possible to arrange the pacer to deliver a back-up pulse with a higher pulse energy than the first pulse. It is also possible to increase the pulse energy in future stimulation pulses if capture is not detected. In order to save battery it is important that the stimulation pulses are not delivered with an unnecessarily high energy. In order to determine a suitable pulse energy, it is known to perform an automatic threshold/capture search. By varying the energy of the stimulation pulses, and by detecting whether capture occurs, it is thus possible to find a threshold value for the stimulation pulse energy. Based on the threshold value, a suitable stimulation pulse energy can be determined.

The detection of capture involves several problems. Different signals from the heart or generated by the pacemaker may interfere with each other, which may make the detection of capture difficult. The evoked response that it is intended to detect may thus be hidden because of other electrical phenomena. It is particularly difficult to detect capture in a bi-ventricular pacer, since in such a pacer there are more delivered and detected signals which may interfere with each other.

A phenomenon in this technical field is "fusion". A fusion may occur when an intrinsic depolarization of the heart takes place simultaneously, or at least almost simultaneously, with a stimulation pulse from the heart stimulating device. Fusion should be avoided when performing a threshold/capture search. In order to avoid such fusion, it is known to temporarily, during such a threshold/capture search, shorten the AV-delay and the PV-delay. Typically, these delays are shortened such that they are set at a predetermined fixed value (e.g. 50 ms and 25 ms, respectively) during such a search.

U.S. Pat. No. 6,498,950 describes a device and method for performing automatic capture/threshold determination in a mono-ventricular pacer. The patent describes a method and a device that instead of using the mentioned fixed AV-delay and the PV-delay during a threshold/capture search, use delays adapted to the particular patient. According to this patent, the device periodically measures the AR/PR conduction times and tabulate and/or otherwise process this data. When an automatic capture/threshold determination occurs, this measured conduction data, which corresponds to the particular patient, is used to adjust the AV/PV delays while minimizing patient discomfort and adverse hemodynamic effects.

SUMMARY OF THE INVENTION

An object of the present invention is to provide an implantable bi-ventricular heart stimulating device with which a threshold/capture search can be carried in an hemodynamically optimal manner. Another object is to provide such a device with which it is possible to adjust certain timing parameters in an optimal manner when performing such a threshold/capture search. A further object it to provide such a device with which it is possible to deliver ventricular pacing pulses to both ventricles even during the time cycles when such a threshold/capture search is carried out. Further objects or advantages of the invention will become clear from the following description and claims.

The above objects are achieved by an implantable heart stimulating device including a control circuit comprising:

at least one memory;

a first atrial sensing and/or pacing circuit, adapted to communicate with a first atrial sensing and/or pacing electrode suited to be positioned in an atrium of a heart, wherein said first atrial sensing and/or pacing circuit is adapted to enable sensing and/or pacing of such an atrium;

a first ventricular sensing circuit, adapted to communicate with a first ventricular sensing electrode suited to be positioned in or at a first ventricle of a heart, wherein said first ventricular sensing circuit is adapted to enable sensing of such a ventricle;

a first ventricular pacing circuit, adapted to communicate with a first ventricular pacing electrode suited to be positioned in or at a first ventricle of a heart, wherein said first ventricular pacing circuit is adapted to enable pacing of such a ventricle;

a second ventricular sensing circuit, adapted to communicate with a second ventricular sensing electrode suited to be positioned in or at a second ventricle of a heart, wherein said second ventricular sensing circuit is adapted to enable sensing of such a ventricle;

a second ventricular pacing circuit, adapted to communicate with a second ventricular pacing electrode suited to be positioned in or at a second ventricle of a heart, wherein said second ventricular pacing circuit is adapted to enable pacing of such a ventricle, said control circuit being arranged to be able to detect an evoked response to a pacing pulse delivered by said first ventricular pacing circuit by sensing, with said first ventricular sensing circuit, within a first time window that follows after a pacing pulse delivered by said first ventricular pacing circuit;

said control circuit being arranged to be able to detect an evoked response to a pacing pulse delivered by said second ventricular pacing circuit by sensing, with said second ventricular sensing circuit, within a second time window that follows after a pacing pulse delivered by said second ventricular pacing circuit;

said control circuit being arranged to be able to operate with time cycles corresponding to normal heart cycles;

said control circuit being arranged to be able to operate, during the normal operation of the device, with a value PV and/or AV, where PV is the time between the sensing with said first atrial sensing and/or pacing circuit and a subsequent pacing pulse, which may also be inhibited, of said first ventricular pacing circuit and AV is the time between the pacing with said first atrial sensing and/or pacing circuit and a subsequent pacing pulse, which may also be inhibited, of said first ventricular pacing circuit;

said control circuit being arranged to, within a time cycle, be able to deliver pacing pulse with both said first ventricular pacing circuit and said second ventricular pacing circuit with a time gap VV, during the normal operation of the device, between a pacing pulse delivered, or inhibited, by said first ventricular pacing circuit and a pacing pulse delivered, or inhibited, by said second ventricular pacing circuit, wherein said time gap VV is $\geq 0$;

said control circuit being arranged to be able to carry out a capture threshold search, by, during a plurality of time cycles, vary the energy of the pacing pulses delivered by said first ventricular pacing circuit and said second ventricular pacing circuit and to detect, with said first ventricular sensing circuit and said second ventricular sensing circuit, respectively, possible evoked responses during said first time window and said second time window, respectively, such that a suitable pulse energy for the pacing pulses delivered by said first ventricular pacing circuit and said second ventricular pacing circuit, respectively, is determined, wherein said control circuit is arranged to determine a time gap $VV_{cts}$, that is to be used instead of VV during said capture threshold search, wherein the determination of said time gap $VV_{cts}$ involves the calculation of a value $$V1R2-ER2-\Delta_{V1R2},$$

where V1R2 is a value which is stored in said memory and which represents the time between a pacing pulse delivered by said first ventricular pacing circuit and a subsequent event sensed by said second ventricular sensing circuit during a time cycle when no pacing pulse is delivered by said second ventricular pacing circuit, ER2 is said second time window and $\Delta_{V1R2}$ is a predetermined value that takes expected variations in V1R2 into account, and wherein $VV_{cts}$, is determined such that
$VV_{cts} \leq V1R2-ER2-\Delta_{V1R2}$ but with the additional condition that $VV_{cts}$ shall not be less than 0 even if V1 R2-ER2-$\Delta_{V1R2}$ is less than 0.

The device is thus configured to calculate a particular time gap $VV_{cts}$. $VV_{cts}$ can thus be used when performing a capture threshold search. If this time gap $VV_{cts}$ is used instead of VV during the capture threshold search, then it is avoided that an R-wave that is being transferred to the second ventricle from the first ventricle interferes with the capture threshold search. Furthermore, this particular $VV_{cts}$ is calculated in order to only reduce VV as much as is necessary in order to perform the capture threshold search. This means that this search can be carried out in a hemodynamically optimal manner. Moreover, it is possible to perform this capture threshold search in the second ventricle even if pacing pulses are delivered by the first ventricular pacing circuit during the same time cycle.

It can be noted that $VV_{cts}$ is never less than 0, i.e. the order in which ventricular pulses are emitted by the first and second ventricular pacing circuits is not reversed.

It should be noted that configuration of a certain circuit to enable sensing and pacing of an atrium or ventricle, does not mean that the circuit actually is connected to an atrium or a ventricle. Instead it means that if the heart stimulating device, in which the circuit in question is included, is actually implanted in a body with suitably located electrodes, and the circuit in question includes those electrodes so as to be able to sense and pace an atrium or a ventricle. Similarly, the expressions relating to atrial or ventricular pacing and sensing circuits or the like only means that these circuits are adapted to be able to sense typical atrial or ventricular events and that they are able to deliver pulses which are of the kind that is typical for stimulating atria or ventricles. A "pacing pulse" or the like is thus a pulse with an energy and morphology which would make it suitable to pace the relevant heart chamber.

It should be noted that the capture threshold search can be performed either simultaneously, i.e. during the same time cycles, for both the first and second ventricles or, alternatively, for one ventricle at a time.

According to one embodiment of the invention, the control circuit is configured such that $VV_{cts}$ is selected as the smallest of the following values:

$$VV \text{ and}$$

$$V1R2-ER2-\Delta_{V1R2},$$

but if $V1R2-ER2-\Delta_{V1R2}$ is less than 0, then $VV_{cts}$ is selected to be 0.

By selecting $VV_{cts}$ in this manner, an optimal $VV_{cts}$ for use during the capture threshold search is determined. VV is thus only reduced if this is necessary in order to avoid the above discussed problem concerning a transferred R-wave to the second ventricle.

According to a further embodiment of the invention, the control circuit is arranged to determine a time $AV_{cts}$, that is to be used instead of AV during the capture threshold search, wherein the determination of the time $AV_{cts}$ involves the calculation of a value $$AR1-ER1-\Delta_{AR1},$$

where AR1 is a value which is stored in the memory and which represents the time between a pacing pulse delivered by the first atrial sensing and/or pacing circuit and a subsequent event sensed by the first ventricular sensing circuit during a time cycle when no pacing pulse is delivered by the first ventricular pacing circuit, ER1 is the first time window and $\Delta_{AR1}$ is a predetermined value that takes expected variations in AR1 into account, and wherein $AV_{cts}$ is determined such that
$AV_{cts} \leq AR1-ER1-\Delta_{AR1}$ but with the additional condition that $AV_{cts}$ shall not be less than a predetermined minimum value for $AV_{cts}$, wherein said minimum value is $\geq 0$, even if $AR1-ER1-\Delta_{AR1}$ is less than the minimum value.

The device thus determines a value $AV_{cts}$ that can be used instead of AV during a capture threshold search. It is thereby avoided that an R-wave in the first ventricle, as a result of a delivered pacing pulse in the atrium, interferes with the capture threshold search.

The determination of the time $AV_{cts}$ can also involve the calculation of a value $AR2-VV_{cts}-ER2-\Delta_{AR2}$, where AR2 is a value which is stored in the memory and which represents the time between a pacing pulse delivered by the first atrial sensing and/or pacing circuit and a subsequent event sensed by the second ventricular sensing circuit during a time cycle when no pacing pulse is delivered by the second ventricular pacing circuit, $VV_{cts}$ is as previously defined, ER2 is said second time window and $\Delta_{AR2}$ is a predetermined value that takes expected variations in AR2 into account, and wherein $AV_{cts}$ is determined such that $AV_{cts} \leq AR2-VV_{cts}-ER2-\Delta_{AR2}$ but with the additional condition that $AV_{cts}$ shall not be less than a predetermined minimum value for $AV_{cts}$, wherein the minimum value is $\geq 0$, even if $AR2-VV_{cts}-ER2-\Delta_{AR2}$ is less than the minimum value.

By using this calculation when determining $AV_{cts}$, it is also avoided that an R-wave in the second ventricle, caused by a previous pacing pulse delivered by the first atrial pacing circuit, interferes with the capture threshold search.

The $AV_{cts}$ can be selected as the smallest of the following values:

$AV$, $AR1-ER1-\Delta_{AR1}$, and $AR2-VV_{cts}-ER2-\Delta_{AR2}$, but with the additional condition that $AV_{cts}$ shall not be less than a predetermined minimum value for $AV_{cts}$ wherein the minimum value is $\geq 0$, even if $AR1-ER1-\Delta_{AR1}$ or $AR2-VV_{cts}-ER2-\Delta_{AR2}$ is less than the minimum value.

In this manner, an optimal $AV_{cts}$ can be determined.

According to one embodiment of the invention, the minimum value for $AV_{cts}$ can be larger than 0 but less than 90 ms, for example, larger than 30 ms but less than 70 ms. Such minimum values for $AV_{cts}$ have been found to be appropriate.

According to a further embodiment of the invention, the control circuit is configured to determine a time $PV_{cts}$, that is to be used instead of PV during said capture threshold search, wherein the determination of said time $PV_{cts}$ involves the calculation of a value $PR1-ER1-\Delta_{PR1}$, where PR1 is a value which is stored in said memory and which represents the time between an event sensed by the first atrial sensing and/or pacing circuit and a subsequent event sensed by the first ventricular sensing circuit during a time cycle when no pacing pulse is delivered by the first ventricular pacing circuit, ER1 is the first time window and $\Delta_{PR1}$ is a predetermined value that takes expected variations in PR1 into account, and wherein $PV_{cts}$ is determined such that $PV_{cts} \leq PR1-ER1-\Delta_{PR1}$ but with the additional condition that $PV_{cts}$ shall not be less than a predetermined minimum value for $PV_{cts}$, wherein the minimum value is $\geq 0$, even if $PR1-ER1-PV_{cts}$ is less than the minimum value.

In this manner, a suitable $PV_{cts}$ can be determined to prevent an R-wave in the first ventricle, caused by a previous sensed atrial event, interferes with the capture threshold search.

Analogously to the above described embodiments in connection with $AV_{cts}$, the determination of the time $PV_{cts}$ can also involve the calculation of a value $PR2-VV_{cts}-ER2-\Delta_{PR2}$, where PR2 is a value which is stored in the memory and which represents the time between an event sensed by the first atrial sensing and/or pacing circuit and a subsequent event sensed by the second ventricular sensing circuit during a time cycle when no pacing pulse is delivered by the second ventricular pacing circuit, $VV_{cts}$ is as previously defined, ER2 is the second time window and $\Delta_{PR2}$ is a predetermined value that takes expected variations in PR2 into account, and wherein $PV_{cts}$ is determined such that $PV_{cts} \leq PR2-VV_{cts}-ER2-\Delta_{PR2}$ but with the additional condition that $PV_{cts}$ shall not be less than a predetermined minimum value for $PV_{cts}$, wherein the minimum value is $\geq 0$, even if $PR2-VV_{cts}-ER2-\Delta_{PR2}$ is less than the minimum value.

In this manner it is possible to determine $PV_{cts}$ such that an R-wave in the second ventricle, caused by a previous sensed atrial event, does not interfere with the capture threshold search.

$PV_{cts}$ can be selected as the smallest of the following values:

$PV$, $PR1-ER1-\Delta_{PR1}$, and $PR2-VV_{cts}-ER2-\Delta_{PR2}$, but with the additional condition that $PV_{cts}$ shall not be less than a predetermined minimum value for $PV_{cts}$, wherein the minimum value is $\geq 0$, even if $PR1-ER1-\Delta_{PR1}$ or $PR2-VV_{cts}-ER2-\Delta_{PR2}$ is less than the minimum value.

In this manner an optimal $PV_{cts}$ can be determined.

According to an embodiment of the invention, the minimum value for $PV_{cts}$ is larger than 0 but less than 60 ms, for example larger than 10 ms but less than 40 ms. Such minimum values for $PV_{cts}$ have been found to be appropriate.

According to a further embodiment of the invention, the control circuit is configured to be able to carry out a search procedure for determining V1R2, and to store the determined value of V1R2 in the memory, such that this stored value can be used when determining $VV_{cts}$ in accordance with any of the above described embodiments. According to this embodiment, the device is thus also configured to be able to determine V1R2. The determined V1R2 can then be used when determining $VV_{cts}$.

The control circuit can be configured such that the procedure for determining V1R2 also involves determining the variation in V1R2 and the determination of an appropriate value for $\Delta_{V1R2}$ and to store the determined value for $\Delta_{V1R2}$ in the memory, such that this stored value can be used when determining $VV_{cts}$ in accordance with any of the above described embodiments. The device can thus also be arranged to automatically determine also $\Delta_{V1R2}$. This determined value can then be used when determining $VV_{cts}$.

The control circuit can be configured such that the procedure for determining V1R2 includes the delivery of a pacing pulse by said first ventricular pacing circuit and the sensing of a subsequent event by the second ventricular sensing circuit during the same time cycle, with the control circuit being configured to carry out this procedure during a part of the time cycle when no atrial events are likely to be sensed by said second ventricular sensing circuit. The control circuit is thus set up to determine V1R2 during a portion of the time cycle when no atrial events are likely to cause sensing in the second ventricular sensing circuit. This means that the control circuit ensures that the detected R-wave actually is caused by a ventricular event in the first ventricle.

Analogously to the above determination of V1R2, the control circuit can be configured to be able to carry out a search procedure for determining AR1, AR2, PR1, PR2, $\Delta_{AR1}$, $\Delta_{AR2}$, $\Delta_{PR1}$ and/or $\Delta_{PR2}$ and to store the determined values in the memory. The device is thus arranged to be able to determine all the different values that are to be used when determining $VV_{cts}$, $AV_{cts}$, and $PV_{cts}$.

According to another aspect of the invention, the invention provides an implantable heart stimulating system comprising:
an implantable heart stimulating device according to any of the preceding embodiments, and
said first atrial sensing and/or pacing electrode,
said first ventricular sensing electrode,
said first ventricular pacing electrode,
said second ventricular sensing electrode, and
said second ventricular pacing electrode,
wherein said electrodes are operationally connected to said device.

The system can also include a number of leads, on which the electrodes are positioned, which leads are connected to the device. The first ventricular sensing electrode can be the same as the first ventricular pacing electrode and the second ventricular sensing electrode can be the same as the second ventricular pacing electrode.

Such a system is thus suitable to be used in a human or animal being.

Another aspect of the invention concerns a method of, in a human or animal being, performing a capture threshold search with the help of a heart stimulating device that, during the normal operation of the device, is set up to operate with times VV, AV and/or PV, ER1 and ER2, where VV is the time between a pacing pulse delivered, or inhibited, to a first ventricle and a pacing pulse delivered, or inhibited, during the same heart cycle, to a second ventricle, wherein said time gap VV is $\geq 0$, where AV is the time between a pacing pulse to a first atrium and a subsequent pacing pulse, which may also be inhibited, to said first ventricle, where PV is the time between a sensed event in said first atrium and a subsequent pacing pulse, which may also be inhibited, to said first ventricle, where ER1 is the evoked response detection window for the first ventricle and where ER2 is the evoked response detection window for the second ventricle. The method includes the following steps:
determine a value V1R2, where V1R2 represents the time between a pacing pulse to the first ventricule and a subsequent event in the second ventricle, during a heart cycle when no pacing pulse is delivered to the second ventricle;
determine $\Delta_{V1R2}$, where $\Delta_{V1R2}$ is a value that takes expected variations in V1R2 into account;
determine a time gap $VV_{cts}$ that is to be used instead of VV during said capture threshold search, such that $VV_{cts} \leq V1R2-ER2-\Delta_{V1R2}$ but with the additional condition that $VV_{cts}$ shall not be less than 0 even if V1R2−ER2−$\Delta_{V1R2}$ is less than 0; and
perform a capture threshold search by using $VV_{cts}$ instead of VV.

The method can involve the selection of $VV_{cts}$ as the smallest of the following values: VV and $$V1R2-ER2-\Delta_{V1R2},$$

but if V1R2−ER2−$\Delta_{V1R2}$ is less than 0, then $VV_{cts}$ is selected to be 0.

With such a method, advantages corresponding to those described above in connection with the device are obtained.

The method can also involve the determination of AR1, AR2, PR1, PR2, $\Delta_{AR1}$, $\Delta_{AR2}$, $\Delta_{PR1}$, and/or $\Delta_{PR2}$ and to use the determined values when determining $AV_{cts}$ and $PV_{cts}$ and, furthermore, to perform a capture threshold search by using $AV_{cts}$ and $PV_{cts}$ instead of AV and PV.

By actually using the determined values for $VV_{cts}$, $AV_{cts}$, and $PV_{cts}$ during a capture threshold search, this search can be performed in an hemodynamically optimal manner.

The method can be performed on a human or animal being suffering from congestive heart failure, for example on a on a human or animal being suffering from a bundle branch block.

DESCRIPTION OF THE PREFERRED EMBODIMENTS

Figure 1:
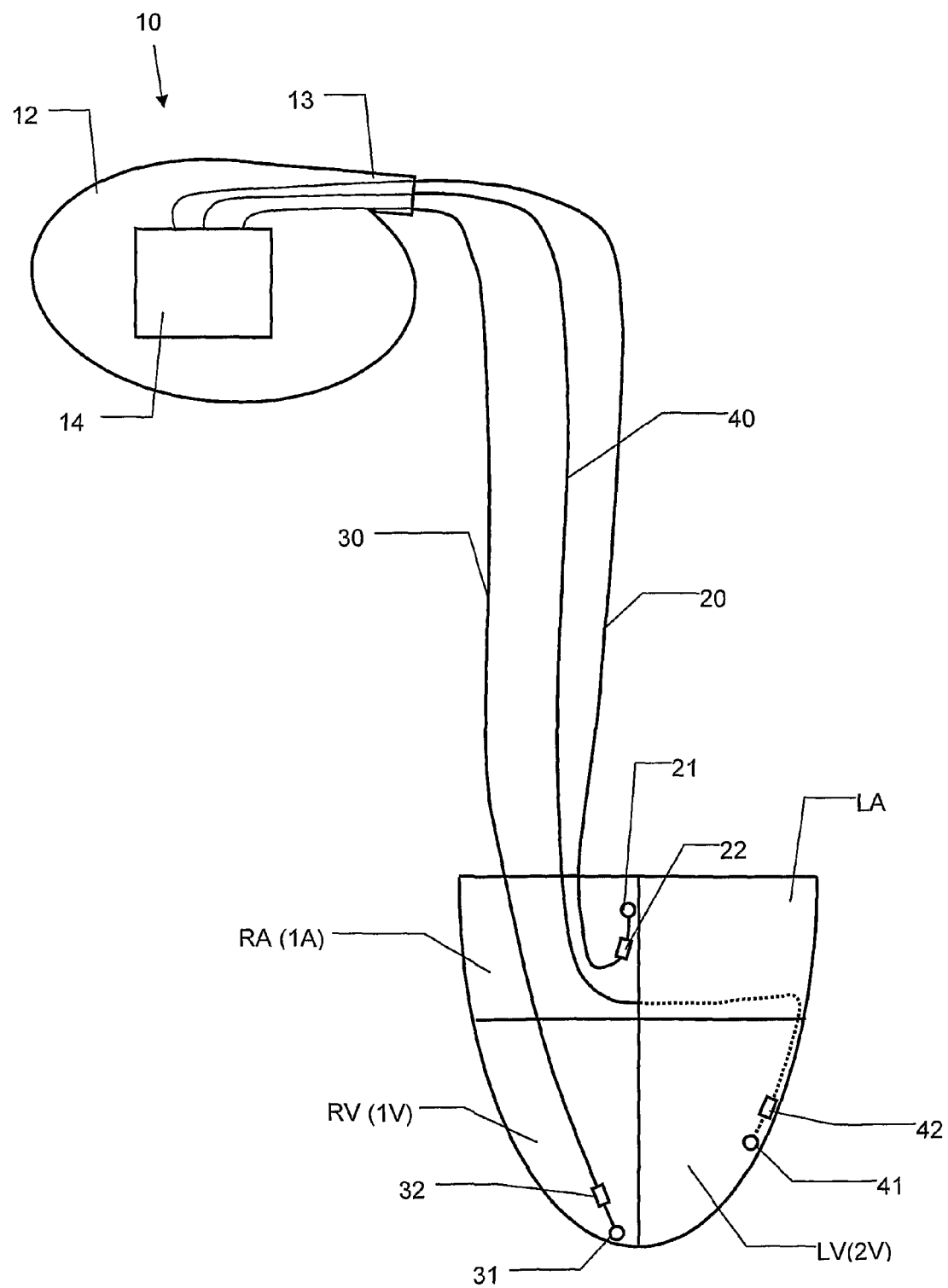
FIG. 1 shows schematically a heart stimulating system with a heart stimulating device connected to leads with sensing and pacing electrodes positioned in a heart.

FIG. 1 shows schematically an implantable heart stimulating device 10 according to the invention. The device 10 comprises a housing 12. The housing 12 includes a control circuit 14. The device 10 comprises a connector portion 13. Via the connector portion 13, the device 10 can be connected to different leads. In FIG. 1 the device 10 is connected to three leads 20, 30 and 40.

The lead 20 includes a pacing and sensing electrode 21, 22. In the shown example, this electrode 21, 22 is a bipolar electrode with a tip portion 21 and a ring portion 22. However, it is within of the scope of the invention that instead unipolar electrodes can be used, as is known to a person skilled in the art. Similarly to the lead 20, the lead 30 includes a pacing and sensing electrode 31, 32 and the lead 40 includes a pacing and sensing electrode 41, 42. The device 10 together with the leads 20, 30, 40 and the electrodes 21, 22; 31, 32; 41 42 constitutes an embodiment of an implantable heart stimulating system according to the invention.

FIG. 1 also schematically illustrates a heart with a right atrium RA, a left atrium LA, a right ventricle RV and a left ventricle LV.

The electrode 21, 22 constitutes a first atrial sensing and/or pacing electrode 21, 22 which is positioned in a first atrium 1A of the heart, according to this embodiment the right atrium RA, in order to enable sensing and/or pacing of this atrium RA.

The electrode 31, 32 constitutes a first ventricular sensing and pacing electrode 31, 32, which is positioned in a first ventricle 1V of the heart, in this embodiment the right ventricle RV. The first ventricular sensing and pacing electrode 31, 32 is adapted to enable sensing and pacing of this first ventricle 1V.

The electrode 41, 42 constitutes a second ventricular sensing and pacing electrode 41, 42, which is positioned at a second ventricle 2V of the heart, in this embodiment the left ventricle LV. The second ventricular sensing and pacing electrode 41, 42 is adapted to enable sensing and pacing of this second ventricle 2V. The lead 40 may for example be introduced via the right atrium RA and the coronary sinus such that the electrode 41, 42 is positioned in for example the middle or great cardiac vein of the heart. How to introduce the lead 40 in this manner is known to a person skilled in the art.

Although not shown in FIG. 1, it is also possible that the system is connected to further leads and/or further electrodes, for example electrodes positioned in order to sense and/or pace the left atrium LA and electrodes designed to enable defibrillation.

Figure 2:
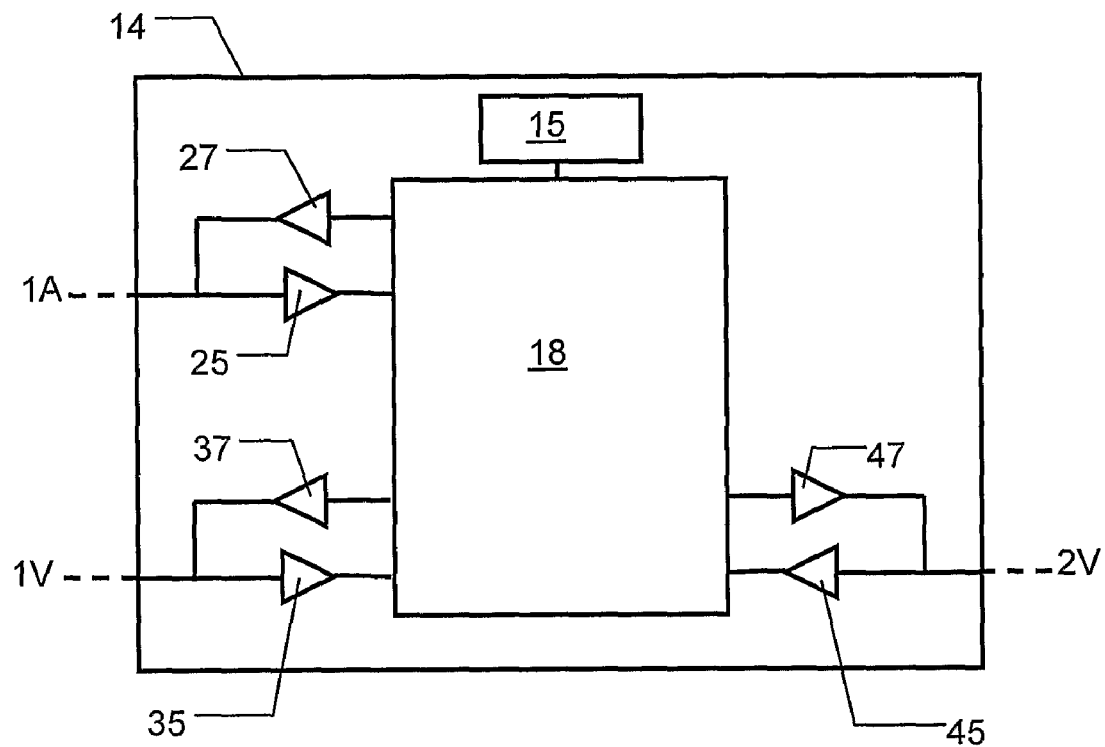
FIG. 2 shows schematically a control circuit which may form part of the device.

FIG. 2 shows schematically the control circuit 14 in some more detail. The control circuit 14 includes a memory 15 connected to a control portion 18. The control circuit 14 includes a first atrial sensing and/or pacing circuit 25, 27. In this embodiment, this circuit 25, 27 includes a sensing circuit 25 and a pacing circuit 27. The first atrial sensing and/or pacing circuit 25, 27 communicates with the first atrial sensing and/or pacing electrode 21, 22 via the lead 20. The first atrial sensing and/or pacing circuit 25, 27 is thus adapted to sense and/or pace an atrium 1A, in this case the right atrium RA.

The control circuit 14 also includes a first ventricular sensing circuit 35 and a first ventricular pacing circuit 37. These circuits 35, 37 communicate with the first ventricular sensing and pacing electrode 31, 32 via the lead 30. The circuits 35, 37 are thus adapted to sense and pace a first ventricle 1V, in this case the right ventricle RV.

The control circuit 14 also includes a second ventricular sensing circuit 45 and a second ventricular pacing circuit 47. These circuits 45, 47 communicate with the second ventricular sensing and pacing electrode 41, 42 via the lead 40. These circuits 45, 47 are adapted to sense and pace a second ventricle 2V, in this case the left ventricle LV.

The control circuit 14 is configured, or programmed, to include several operational features. The control circuit is thus arranged to be able to detect an evoked response to a pacing pulse delivered by said first ventricular pacing circuit 37 by sensing, with said first ventricular sensing circuit 35, within a first time window ER1 that follows after a pacing pulse delivered by said first ventricular pacing circuit 37.

Similarly, the control circuit 14 is also configured to be able to detect an evoked response to a pacing pulse delivered by said second ventricular pacing circuit 47 by sensing, with said second ventricular sensing circuit 45, within a second time window ER2 that follows after a pacing pulse delivered by said second ventricular pacing circuit 47.

The basic design for a pacer to sense evoked response is known to those skilled in the art. The first time window ER1 may for example be set to begin 5 ms to 30 ms, for example 15 ms, after the delivery of a pacing pulse by the first ventricular pacing circuit 37. The length of the first time window ER1 may for example be 30 ms to 70 ms, for example 50 ms. Analogously, the second time window ER2 can for example be set to begin 5 ms to 30 ms, for example 15 ms, after the delivery of a pacing pulse by the second ventricular pacing circuit 47. The length of the second time window ER2 may for example be 30 ms to 70 ms, for example 50 ms. It should be noted that the first ER1 and second ER2 time windows do not necessarily have to have the same length and they do not necessarily have to start or end the same the time period after the respective delivered pacing pulse.

As is normal in a heart stimulating device, the first ventricular sensing circuit 35 and the second ventricular sensing circuit 45 are also able to sense events typical for an R-wave (QRS-complex) in the respective ventricle.

Figure 3:
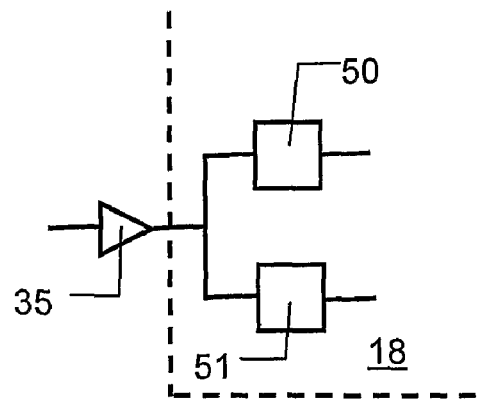
FIG. 3 shows schematically a somewhat more detailed illustration of part of the control circuit of FIG. 2.

FIG. 3 shows schematically a part of the control circuit 14 in some more detail. FIG. 3 illustrates that the first ventricular sensing circuit 35 is connected to an evoked response detection logic 50 and an R-wave detection logic 51. The detection logics 50 and 51 can be seen to form part of the control portion 18 illustrated in FIG. 2. Preferably, similar detection logics are of course arranged also for the second ventricular sensing circuit 45. The detection logic 50 is thus optimized to sense an evoked response and the detection logic 51 is optimized to detect an R-wave.

As is also normal in a heart stimulating device, the first atrial sensing and/or pacing circuit 25, 27 is also arranged to be able to detect events typical for a P-wave.

The control circuit 14 is arranged to be able to operate with time cycles corresponding to normal heart cycles. Such an operation is normal for an implantable heart stimulating device. The time cycles are determined by preset timer intervals which also may depend on detected signals The control circuit 14 is also arranged to be able to operate, during the normal operation of the device 10, with a value PV and/or AV. PV is the time between the sensing with the first atrial sensing and/or pacing circuit 25, 27 and a subsequent pacing pulse, which may also be inhibited, of the first ventricular pacing circuit 37. AV is the time between the pacing with said first atrial sensing and/or pacing circuit 25, 27 and a subsequent pacing pulse, which may also be inhibited, of said first ventricular pacing circuit 37. It is well known to those skilled in the art how an implantable heart stimulating device is set up in order to operate with PV and AV intervals. It is also known that the delivery of pacing pulses can be inhibited.

The control circuit 14 is also configured to be able to deliver, within a time cycle, pacing pulse with both said first ventricular pacing circuit 37 and said second ventricular pacing circuit 47 with a time gap VV, during the normal operation of the device 10, between a pacing pulse delivered, or inhibited, by the first ventricular pacing circuit 37 and a pacing pulse delivered, or inhibited, by the second ventricular pacing circuit 47, wherein the time gap VV is $\geq 0$. A typical value of VV can be between 0 ms and 80 ms.

In the present case, the AV and PV intervals are thus defined in relation to the ventricular pacing circuit that is paced (or inhibited) first (if VV is not equal to 0; if VV is 0 then, of course, the first and second ventricular pacing circuits operate simultaneously). With this definition, VV cannot be less than 0. The ventrical that is referred to as the first ventricle 1V is thus, in the present embodiment, the ventricle that is paced (or inhibited) first, if VV is not equal to 0. This ventricle can be either the left LV or the right RV ventricle depending on the particular case. However, the present invention is intended to extend also to the situation where some other definition of the PV and AV intervals is used, e.g. if VV can be negative.

The control circuit 14 is also arranged to be able to carry out a capture threshold search, by during a number of time cycles, vary the energy of the pacing pulses delivered by the first ventricular pacing circuit 37 and the second ventricular pacing circuit 47 and to detect, with the first ventricular sensing circuit 35 and the second ventricular sensing circuit 45, respectively, possible evoked responses during the first time window ER1 and the second time window ER2, respectively, such that a suitable pulse energy for the pacing pulses delivered by the first ventricular pacing circuit 37 and the second ventricular pacing circuit 47, respectively, is determined. The suitable pulse energy can be selected somewhat higher than the actually measured threshold, in order to have a safety margin. According to the present invention, the capture threshold search can either be carried simultaneously (during the same time cycles) for both the first and second channels, or, alternatively, in one channel at a time. The device 10 can be configured to perform a capture, threshold search periodically, for example once a day, but it is also possible that the device 10 is set up to perform such a search when a predetermined number of lack of capture beats have been detected.

As has been explained above, it may be necessary to reduce the different times AV, PV during a capture threshold search in order to avoid fusion. According to the present invention this is done in an optimal manner. Furthermore, according to the present invention, also VV is reduced, if necessary, in an optimal manner when a capture threshold search is being carried out.

When a capture threshold search is to be carried out, first some intrinsic conduction times have to be determined and stored in the memory. This can be done just before the capture threshold search is carried out. However, it is also possible to determine the intrinsic conduction times at an earlier stage.

First some abbreviations that are used below will be explained.

V1R2 is a value which represents the time between a pacing pulse delivered by said first ventricular pacing circuit 37 and a subsequent event sensed by said second ventricular sensing circuit 45 during a time cycle when no pacing pulse is delivered by said second ventricular pacing circuit 47. This time thus represents the time it takes for a paced R-wave in the first ventricle 1V to be transferred to the second ventricle 2V.

$\Delta_{V1R2}$ is a value that takes expected variations in V1R2 into account.

AR1 is a value which represents the time between a pacing pulse delivered by said first atrial sensing and/or pacing circuit 25, 27 and a subsequent event sensed by the first ventricular sensing circuit 35 during a time cycle when no pacing pulse is delivered by said first ventricular pacing circuit 37. AR1 thus represents the conduction time from a paced event in the atrium 1A to a detected R-wave in the first ventricle 1V.

$\Delta_{AR1}$, is a predetermined value that takes expected variations in AR1 into account.

AR2 is a value which represents the time between a pacing pulse delivered by the first atrial sensing and/or pacing circuit 25, 27 and a subsequent event sensed by the second ventricular sensing circuit 45 during a time cycle when no pacing pulse is delivered by said second ventricular pacing circuit 47. AR2 thus represents the conduction time from a paced event in the atrium 1A to a detected R-wave in the second ventricle 2V.

$\Delta_{AR2}$ is a predetermined value that takes expected variations in AR2 into account.

PR1 is a value which represents the time between an event sensed by the first atrial sensing and/or pacing circuit 25, 27 and a subsequent event sensed by the first ventricular sensing circuit 35 during a time cycle when no pacing pulse is delivered by the first ventricular pacing circuit 37. PR1 thus represents the conduction time from a sensed event in the atrium 1A to a detected R-wave in the first ventricle 1V.

$\Delta_{PR1}$ is a predetermined value that takes expected variations in PR1 into account.

PR2 is a value which represents the time between an event sensed by the first atrial sensing and/or pacing circuit 25, 27 and a subsequent event sensed by the second ventricular sensing circuit 45 during a time cycle when no pacing pulse is delivered by the second ventricular pacing circuit 47. PR2 thus represents the conduction time from a sensed event in the atrium 1A to a detected R-wave in the second ventricle 2V, $\Delta_{PR2}$ is a predetermined value that takes expected variations in PR2 into account.

The device 10 is thus configured to determine intrinsic conduction times.

The control circuit 14 is arranged to carry out a search procedure for determining V1R2, and to store the determined value of V1R2 in the memory 15. This procedure includes the delivery of a pacing pulse with the first ventricular pacing circuit 37 and the sensing of a subsequent event by the second ventricular sensing circuit 45 during the same time cycle. The control circuit 14 is arranged to carry out this procedure during a part of the time cycle when no atrial events are likely to be sensed by the second ventricular sensing circuit 45, i.e. the part of the time cycle when no sensing in the second ventricle 2V caused by a previous atrial event is likely to occur. This procedure also involves determining the variation in V1R2 and the determination of an appropriate value for $\Delta_{V1R2}$ and to store the determined value for $\Delta_{V1R2}$ in the memory 15. The determined value of $\Delta_{V1R2}$ thus can represent, for example, the mean value of the conduction times V1R2 measured during a number of heart cycles, for example 10 heart cycles. $\Delta_{V1R2}$ can be determined statistically and can thus represent some measure of the variation in V1R2. For example, $\Delta_{V1R2}$ can be selected such that an expected value of V1R2 with a certain probability, for example 98% percent probability, will fall within the range V1R2±$\Delta_{V1R2}$.

Analogously, the control circuit 14 is arranged to carry out a search procedure for determining AR1, and to store the determined value of AR1 in the memory 15. The procedure for determining AR1 includes the delivery of a pacing pulse with the first atrial sensing and/or pacing circuit 25, 27 and the sensing of a subsequent event with the first ventricular sensing circuit 35 during the same time cycle. The control circuit 14 is arranged such that no pacing pulse is delivered by the first ventricular pacing circuit 37 during this time cycle. The procedure for determining AR1 also involves determining the variation in AR1 and the determination of an appropriate value for $\Delta_{AR1}$ and to store the determined value for $\Delta_{AR1}$ in the memory 15.

Analogously, the control circuit 14 is arranged to carry out a search procedure for determining AR2, and to store the determined value of AR2 in the memory 15. The procedure for determining AR2 includes the delivery of a pacing pulse with the first atrial sensing and/or pacing circuit 25, 27 and the sensing of a subsequent event with the second ventricular sensing circuit 45 during the same time cycle. The control circuit 14 is arranged such that no pacing pulse is delivered by the second ventricular pacing circuit 47 during this time cycle. This procedure also involves determining the variation in AR2 and the determination of an appropriate value for $\Delta_{AR2}$ and to store the determined value for $\Delta_{AR2}$ in the memory 15, Analogously, the control circuit 14 is arranged to carry out a search procedure for determining PR1, and to store the determined value of PR1 in the memory 15. This procedure includes the sensing with the first atrial sensing and/or pacing circuit 25, 27 and the sensing of a subsequent event with the first ventricular sensing circuit 35 during the same time cycle. No pacing pulse is delivered by the first ventricular pacing circuit 37 during this time cycle. The procedure for determining PR1 also involves determining the variation in PR1 and the determination of an appropriate value for $\Delta_{PR1}$ and to store the determined value for $\Delta_{PR1}$ in the memory 15.

The control circuit 14 is also arranged to carry out a search procedure for determining PR2, and to store the determined value of PR2 in the memory 15. This procedure includes the sensing with the first atrial sensing and/or pacing circuit 25, 27 and the sensing of a subsequent event with the second ventricular sensing circuit 45 during the same time cycle. The control circuit 14 is arranged such that no pacing pulse is delivered by the second ventricular pacing circuit 47 during this time cycle. This procedure also involves determining the variation in PR2 and the determination of an appropriate value for $\Delta_{PR2}$ and to store the determined value for $\Delta_{PR2}$ in the memory 15.

AR1, AR2, PR1 and PR2 can be determined as a mean or average value similarly to the determination of V1R2 described above. Also the procedures for determining $\Delta_{AR1}$, $\Delta_{AR2}$, $\Delta_{PR1}$ and $\Delta_{PR2}$ can be performed in a similar manner to that described above in connection with the determination of $\Delta_{V1R2}$.

As noted above, no pacing pulse is delivered by certain pacing circuits during the time cycles when the different intrinsic conduction times are determined. It is of course also possible to deliver a pacing pulse during the same time cycle if such a pacing pulse is delivered during a part of the time cycle when it will not interfere with the detection of the intrinsic conduction. This can be, for example, achieved if certain pacing intervals, such as AV or PV, are increased during such determination of intrinsic conduction times.

Furthermore, the control circuit 14 is configured to determine a time gap $VV_{cts}$, that is to be used instead of VV during the capture threshold search. $VV_{cts}$ is hereby selected as the smallest of the following values;

VV and

V1R2−ER2−$\Delta_{V1R2}$, but if V1R2−ER2−, $\Delta_{V1R2}$ is less than 0, then $VV_{cts}$ is selected to be 0.

Furthermore, the control circuit 14 is arranged to determine a time $AV_{cts}$, that is to be used instead of AV during the capture threshold search. $AV_{cts}$ is selected as the smallest of the following values:

AV,

AR1−ER1−$\Delta_{AR1}$, and

AR2−$VV_{cts}$−ER2−$\Delta_{AR2}$ but with the additional condition that $AV_{cts}$ shall not be less than a predetermined minimum value for $AV_{cts}$, wherein the minimum value is $\geq 0$, even if AR1−ER1−$\Delta_{AR1}$ or AR2−$VV_{cts}$−ER2−$\Delta_{AR2}$ is less than the minimum value. The minimum value for $AV_{cts}$ can for example be 50 ms.

Moreover, the control circuit 14 is configured to determine a time $PV_{cts}$, that is to be used instead of PV during the capture threshold search. $PV_{cts}$ is selected as the smallest of the following values:

PV,

PR1−ER1−$\Delta_{PR1}$, and

PR2−$VV_{cts}$,−ER2−$\Delta_{PR2}$, but with the additional condition that $PV_{cts}$ shall not be less than a predetermined minimum value for $PV_{cts}$, wherein the minimum value is $\geq 0$, even if PR1−ER1−$\Delta_{PR1}$ Or PR2−$VV_{cts}$−ER2−$\Delta_{PR2}$ is less than the minimum value. The minimum value for $PV_{cts}$ can for example be 25 ms.

Finally, the control circuit 14 is configured to be able to use the determined values for $VV_{cts}$, $AV_{cts}$ and $PV_{cts}$, instead of VV, AV and PV when actually performing a capture threshold search.

The invention also provides a method of, in a human or animal being, performing a capture threshold search with the help of a heart stimulating device.

Figure 4:
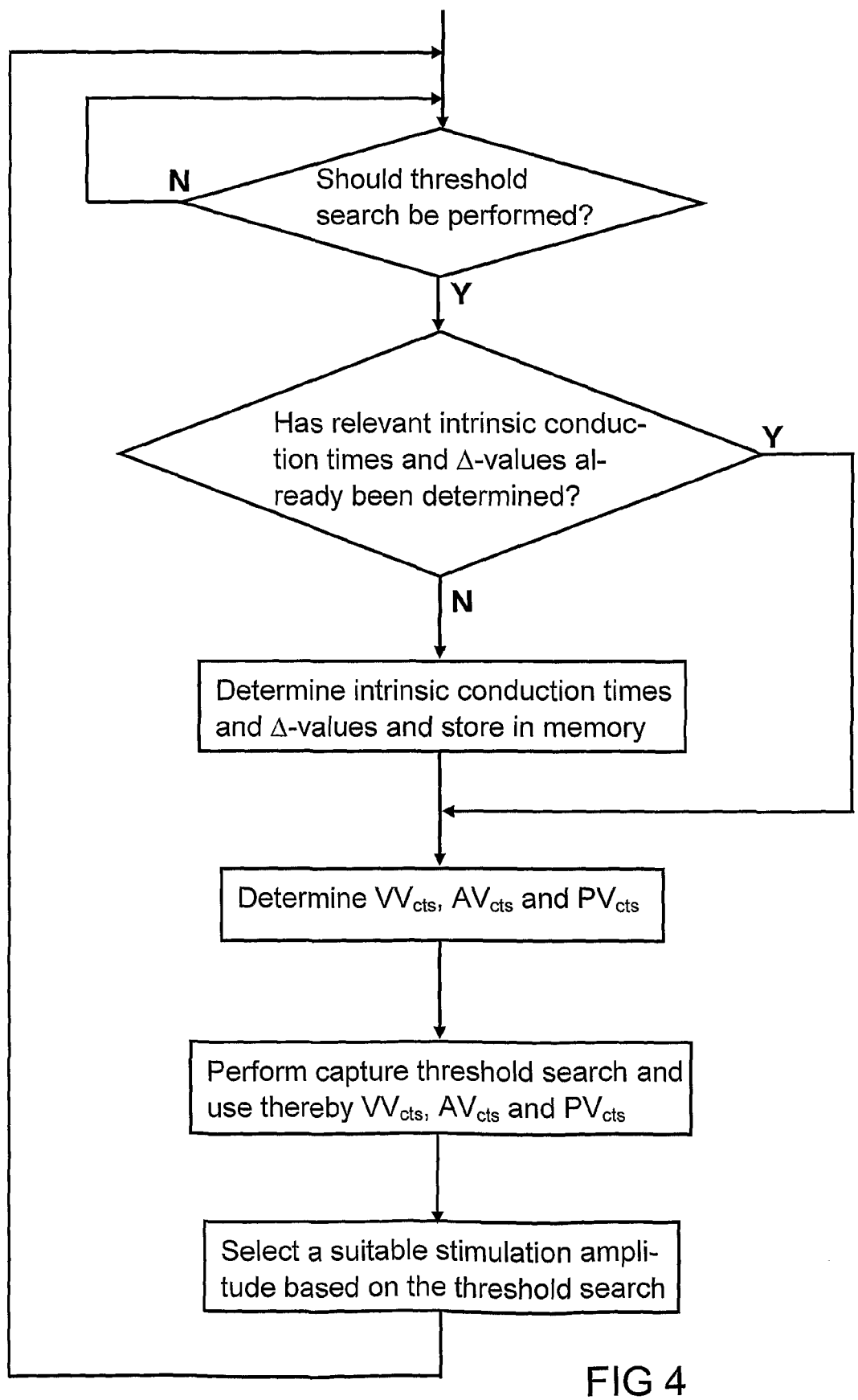
FIG. 4 illustrates schematically a method according to the invention.

FIG. 4 discloses very schematically a flow chart for such a method. At the same time, this figure illustrates schematically how a device 10 according to the invention can operate.

The device normally operates with times VV, AV and/or PV, ER1 and ER2 as explained above.

A capture threshold search can be performed at regular intervals, for example once a day, or when a certain number of loss of capture has been detected.

If a capture threshold search is to be carried out, then first the values for V1R2, AR1, AR2, PR1, PR2, $\Delta_{V1R2}$, $\Delta_{AR1}$, $\Delta_{AR2}$, $\Delta_{PR1}$ and $\Delta_{PR2}$ are determined. These values can for example be determined as explained above or in any other suitable manner. For example, if any of these values is known before with sufficient accuracy, then it may not be necessary to perform a special search for finding out this value. Moreover, these values can either be determined just before the capture threshold search is performed, or these values can have been determined earlier.

Thereafter a the times $VV_{cts}$, $AV_{cts}$, and $PV_{cts}$, that that are to be used instead of VV, AV and PV, respectively, during said capture threshold search are determined. These times can be determined as follows.

$VV_{cts}$ is selected as the smallest of the following values:

VV and

V1R2−ER2−$\Delta_{V1R2}$, but if V1R2−ER2−$\Delta_{V1R2}$ is less than 0, then $VV_{cts}$ is selected to be 0.

$AV_{cts}$ is selected as the smallest of the following values:

AV,

AR1−ER1−$\Delta_{AR1}$, and

AR2−$VV_{cts}$−ER2−$\Delta_{AR2}$, but with the additional condition that $AV_{cts}$ shall not be less than a predetermined minimum value for $AV_{cts}$, for example 50 ms, even if AR1−ER1−$\Delta_{AR1}$, or AR2−$VV_{cts}$, −ER2−$\Delta_{AR2}$ is less than 50 ms.

$PV_{cts}$ is selected as the smallest of the following values:

PV,

PR1−ER1−$\Delta_{PR1}$, and

PR2−$VV_{cts}$−ER2−$\Delta_{PR2}$, but with the additional condition that $PV_{cts}$ shall not be less than a predetermined minimum value for $PV_{cts}$, for example 25 ms, even if PR1−ER1−$\Delta_{PR1}$ or PR2−$VV_{cts}$−ER2−$\Delta_{PR2}$ is less than 25 ms.

The method then also includes the step of actually performing a capture threshold search by using $VV_{cts}$, $AV_{cts}$ and $PV_{cts}$ instead of W, AV and PV. Based on the capture threshold search, a suitable stimulation amplitude can be selected. The stimulation amplitude is set such that a certain safety margin is achieved How to select a certain safety margin is known from prior devices that operate with an evoked response detection.

The method can be performed on a human or animal being suffering from congestive heart failure, for example on a on a human or animal being suffering from a bundle branch block.

It should be noted that it is of course only necessary to determine and use those values which are essential for the operation in the particular case. For example, if sensing in the atrium is not used, then it is of course not necessary to determine $PV_{cts}$ or the values needed for determining $PV_{cts}$.

Although modifications and changes may be suggested by those skilled in the art, it is the intention of the inventors to embody within the patent warranted heron all changes and

We claim as our invention:

1. An implantable heart stimulating device comprising:
   at least one memory;
   a first atrial sensing and/or pacing circuit configured to communicate with a first atrial sensing and/or pacing electrode configured to be positioned in an atrium of a heart, said first atrial sensing and/or pacing circuit being configured to enable sensing and/or pacing of the atrium;
   a first ventricular sensing circuit configured, to communicate with a first ventricular sensing electrode configured to be positioned in or at a first ventricle of said heart, said first ventricular sensing circuit being configured to enable sensing of the first ventricle;
   a first ventricular pacing circuit configured to communicate with a first ventricular pacing electrode configured to be positioned in or at the first ventricle of said heart, said first ventricular pacing circuit being configured to enable pacing of the first ventricle;
   a second ventricular sensing circuit configured to communicate with a second ventricular sensing electrode configured to be positioned in or at a second ventricle of said heart, said second ventricular sensing circuit being configured to enable sensing of the second ventricle;
   a second ventricular pacing circuit configured to communicate with a second ventricular pacing electrode configured to be positioned in or at the second ventricle of said heart, said second ventricular pacing circuit being configured to enable pacing of the second ventricle;
   a control circuit configured to detect an evoked response to a pacing pulse delivered by said first ventricular pacing circuit by sensing, with said first ventricular sensing circuit, within a first time window that follows after a pacing pulse delivered by said first ventricular pacing circuit;
   a control circuit being configured to detect an evoked response to a pacing pulse delivered by said second ventricular pacing circuit by sensing, with said second ventricular sensing circuit, within a second time window that follows after a pacing pulse delivered by said second ventricular pacing circuit; said control circuit being configured to operate with time cycles corresponding to normal heart cycles;
   said control circuit being configured to operate, during the normal operation of the device, with a value PV and/or AV, where PV is the time between the sensing with said first atrial sensing and/or pacing circuit and a subsequent pacing pulse, which may also be inhibited, of said first ventricular pacing circuit and AV is the time between the pacing with said first atrial sensing and/or pacing circuit and a subsequent pacing pulse, which may also be inhibited, of said first ventricular pacing circuit;
   said control circuit being configured to deliver, within a time cycle pacing pulse with both said first ventricular pacing circuit and said second ventricular pacing circuit with a time gap VV, during the normal operation of the device, between a pacing pulse delivered, or inhibited, by said first ventricular pacing circuit and a pacing pulse delivered, or inhibited, by said second ventricular pacing circuit, wherein said time gap VV is $\geq 0$;
   said control circuit being configured to execute a capture threshold search, by, during a plurality of time cycles, vary the energy of the pacing pulses delivered by said first ventricular pacing circuit and said second ventricular pacing circuit and to detect, with said first ventricular sensing circuit and said second ventricular sensing circuit, respectively, possible evoked responses during said first time window and said second time window, respectively, and to determine a suitable pulse energy for the pacing pulses delivered by said first ventricular pacing circuit and said second ventricular pacing circuit, respectively;
   said control circuit being configured to determine a time gap $VV_{cts}$, that is to be used instead of VV during said capture threshold search, by calculating a value $V1R2-ER2-\Delta_{V1R2}$,
   where V1R2 is a value which is stored in said memory and which represents the time between a pacing pulse delivered by said first ventricular pacing circuit and a subsequent event sensed by said second ventricular sensing circuit during a time cycle when no pacing pulse is delivered by said second ventricular pacing circuit, ER2 is said second time window, and $\Delta_{V1R2}$ is a predetermined value that takes expected variations in V1R2 into account,
   and by setting $VV_{cts}$ such that $VV_{cts} < V1R2-ER2-\Delta_{V1R2}$ with the additional condition that $VV_{cts}$ shall not be less than 0 even if $V1R2-ER2-\Delta_{V1R2}$ is less than 0.

2. An implantable heart stimulating device according to claim 1, wherein the control circuit is configured to set $VV_{cts}$ as the smallest of the following values:

VV and $V1R2-ER2-\Delta_{V1R2}$, but if $V1R2-ER2-\Delta_{V1R2}$ is less than 0, then $VV_{cts}$ is selected to be 0.

3. An implantable heart stimulating device according to claim 1, wherein the control circuit is configured to determine a time $AV_{cts}$, that is to be used instead of AV during said capture threshold search, by calculating a value $AR1-ER1-\Delta_{AR1}$, where AR1 is a value which is stored in said memory and which represents the time between a pacing pulse delivered by said first atrial sensing and/or pacing circuit (25, 27) and a subsequent event sensed by said first ventricular sensing circuit (35) during a time cycle when no pacing pulse is delivered by said first ventricular pacing circuit (37), ER1 is said first time window and $\Delta_{AR1}$ is a predetermined value that takes expected variations in AR1 into account,
   and wherein $AV_{cts}$ is set such that
   $AV_{cts} \leq AR1-ER1-\Delta_{AR1}$ but with the additional condition that $AV_{cts}$ shall not be less than a predetermined minimum value for $AV_{cts}$, wherein said minimum value is $\geq 0$, even if $AR1-ER1-\Delta_{AR1}$ is less than said minimum value.

4. An implantable heart stimulating device according to claim 3, wherein the determination of said time $AV_{cts}$ also involves the calculation of a value $AR2-VV_{cts}-ER2-\Delta_{AR2}$, where AR2 is a value which is stored in said memory and which represents the time between a pacing pulse delivered by said first atrial sensing and/or pacing circuit and a subsequent event sensed by said second ventricular sensing circuit during a time cycle when no pacing pulse is delivered by said second ventricular pacing circuit, $VV_{cts}$ is as previously defined, ER2 is said second time window and $\Delta_{AR2}$ is a predetermined value that takes expected variations in AR2 into account, and wherein said control circuit sets $AV_{cts}$ such that $AV_{cts} \leq AR2-VV_{cts}-ER2-\Delta_{AR2}$ but with the additional condition that $AV_{cts}$ shall not be less than a predetermined minimum value for $AV_{cts}$, wherein said minimum value is $\geq 0$, even if $AR2-VV_{cts}-ER2-\Delta_{AR2}$ is less than said minimum value.

5. An implantable heart stimulating device according to claim 4, wherein the control circuit is configured to set $AV_{cts}$ as the smallest of the following values:

AV, $AR1-ER1-\Delta_{AR1}$, and $AR2-VV_{cts}-ER2-\Delta_{AR2}$, but with the additional condition that $AV_{cts}$ shall not be less than a predetermined minimum value for $AV_{cts}$, wherein said minimum value is $\geq 0$, even if $AR1-ER1-\Delta_{AR1}$ or $AR2-VV_{cts}-ER2-\Delta_{AR2}$ is less than said minimum value.

6. An implantable heart stimulating device according to claim 3, wherein the circuit employs a minimum value for $AV_{cts}$ that is larger than 0 but less than 90 ms.

7. An implantable heart stimulating device according to claim 6, wherein the control circuit employs a minimum value for $AV_{cts}$ that is larger than 30 ms but less than 70 ms.

8. An implantable heart stimulating device according to claim 1, wherein the control circuit is configured to determine a time $PV_{cts}$, that is to be used instead of PV during said capture threshold search, control circuit determining said time $PV_{cts}$ calculating a value $PR1-ER1-\Delta_{PR1}$, where PR1 is a value which is stored in said memory and which represents the time between an event sensed by said first atrial sensing and/or pacing circuit and a subsequent event sensed by said first ventricular sensing circuit during a time cycle when no pacing pulse is delivered by said first ventricular pacing circuit, ER1 is said first time window and $\Delta_{PR1}$ is a predetermined value that takes expected variations in PR1 into account, and wherein the control circuit sets $PV_{cts}$ such that $PV_{cts} \leq PR1-ER1-\Delta_{PR1}$ but with the additional condition that $PV_{cts}$ shall not be less than a predetermined minimum value for $PV_{cts}$, wherein said minimum value is $\geq 0$, even if $PR1-ER1-\Delta_{PR1}$ is less than said minimum value.

9. An implantable heart stimulating device according to claim 8, wherein the control circuit determines said time $PV_{cts}$ by also calculating a value $PR2-VV_{cts}-ER2-\Delta_{PR2}$, where PR2 is a value which is stored in said memory and which represents the time between an event sensed by said first atrial sensing and/or pacing circuit and a subsequent event sensed by said second ventricular sensing circuit during a time cycle when no pacing pulse is delivered by said second ventricular pacing circuit, VVcts is as previously defined, ER2 is said second time window and $\Delta_{PR2}$ is a predetermined value that takes expected variations in PR2 into account, and wherein $PV_{cts}$ is determined such that $PV_{cts} \leq PR2-VV_{cts}-ER2-\Delta_{PR2}$ but with the additional condition that $PV_{cts}$ shall not be less than a predetermined minimum value for $PV_{cts}$, wherein said minimum value is $\geq 0$, even if $PR2-VV_{cts}-ER2-\Delta_{PR2}$ is less than said minimum value.

10. An implantable heart stimulating device according to claim 9, wherein the control circuit is configured to set $PV_{cts}$ as the smallest of the following values:

PV, $PR1-ER1-\Delta_{PR1}$, and $PR2-VV_{cts}, -ER2-\Delta_{PR2}$, but with the additional condition that $PV_{cts}$ shall not be less than a predetermined minimum value for $PV_{cts}$, wherein said minimum value is $\geq 0$, even if $PR1-ER1-\Delta_{PR1}$ or $PR2-VV_{cts}, -ER2-\Delta_{PR2}$ is less than said minimum value.

11. An implantable heart stimulating device according to claim 8, wherein the control circuit employs a minimum value for $PV_{cts}$ that is larger than 0 but less than 60 ms.

12. An implantable heart stimulating device according to claim 11, wherein the control circuit employs a minimum value for $PV_{cts}$, that is larger than 10 ms but less than 40 ms.

13. An implantable heart stimulating device according to claim 1, wherein the control circuit is configured to execute a search procedure for determining V1R2, and to store a value of V1R2 determined in said search procedure in said memory use when determining $VV_{cts}$.

14. An implantable heart stimulating device according to claim 13, wherein the control circuit is configured in the procedure for determining V1R2, to also determine a variation in V1R2 and to determine a value for $\Delta_{V1R2}$ and to store the determined value for $\Delta_{V1R2}$ in said memory, for use when determining $VV_{cts}$.

15. An implantable heart stimulating device according to claim 13, wherein the control circuit is configured to execute the procedure for determining by causing delivery of a pacing pulse by said first ventricular pacing circuit and the sensing of a subsequent event by said second ventricular sensing circuit during the same time cycle, and wherein the control circuit is configured to execute said procedure during a part of the time cycle when no atrial events are likely to be sensed by said second ventricular sensing circuit.

16. An implantable heart stimulating device according to claim 3, wherein the control circuit is configured to execute a search procedure for determining AR1, and to store a value determined in said search procedure of AR1 in said memory, for use when determining $AV_{cts}$.

17. An implantable heart stimulating device according to claim 16, wherein the control circuit is configured in the procedure for determining AR1, to also determine a variation in AR1 and to determine a value for $\Delta_{AR1}$ and to store the determined value for $\Delta_{AR1}$, in said memory, for use when determining $AV_{cts}$.

18. An implantable heart stimulating device according to claim 16, wherein the control circuit is to execute the procedure for determining AR1 by causing delivery of a pacing pulse by said a first atrial sensing and/or pacing circuit and sensing of a subsequent event by said first ventricular sensing circuit during the same time cycle, and the control circuit is configured to cause no pacing pulse to be delivered by said first ventricular pacing circuit during this time cycle.

19. An implantable heart stimulating device according to claim 4, wherein the control circuit is configured to execute a search procedure for determining AR2, and to store the determined value of AR2 in said memory, for use when determining $AV_{cts}$.

20. An implantable heart stimulating device according to claim 19, wherein the control circuit is configured, in the procedure for determining AR2, to also determine a variation in AR2 and to determine a value for $\Delta_{AR2}$ and to store the value for $\Delta_{AR2}$ determined in said procedure in said memory, for use when determining $AV_{cts}$.

21. An implantable heart stimulating device according to claim 19, wherein the control circuit is configured in the procedure for determining AR2, to cause delivery of a pacing pulse by said first atrial sensing and/or pacing circuit and sensing of a subsequent event by said second ventricular sensing circuit during the same time cycle, and wherein the control circuit is configured to cause no pacing pulse to be delivered by said second ventricular pacing circuit during this time cycle.

22. An implantable heart stimulating device according to claim 8, wherein the control circuit is configured to execute a search procedure for determining PR1, and to store a value of PR1 determined in said search procedure in said memory for use when determining $PV_{cts}$.

23. An implantable heart stimulating device according to claim 22, wherein the control circuit is configured in the procedure for determining PR1 to also determine variation in PR1 and to determine a value for $\Delta_{PR1}$ and to store the determined value for $\Delta_{PR1}$ in said memory for use when determining $PV_{cts}$.

24. An implantable heart stimulating device according to claim 22, wherein the control circuit is configured in the procedure for determining PR1, to sense with said first atrial sensing and/or pacing circuit and to sense a subsequent event by said first ventricular sensing circuit during the same time cycle, and wherein the control circuit is configured to cause no pacing pulse to be delivered by said first ventricular pacing circuit during this time cycle.

25. An implantable heart stimulating device according to claim 9, wherein the control circuit is configured to execute a search procedure for determining PR2, and to store a value of PR2 determined in search procedures in said memory for use when determining $PV_{cts}$.

26. An implantable heart stimulating device according to claim 25, wherein the control circuit is configured in the procedure for determining PR2, to also determine a variation in PR2 and to determine a value for $\Delta_{PR2}$ and to store the determined value for $\Delta_{PR2}$ in said memory for use when determining $PV_{cts}$.

27. An implantable heart stimulating device according to claim 25, wherein the control circuit is configured in the procedure for determining PR2, to sense with said first atrial sensing and/or pacing circuit and to sense a subsequent event by said second ventricular sensing circuit during the same time cycle, and wherein the control circuit is configured to cause no pacing pulse to be delivered by said second ventricular pacing circuit during this time cycle.

28. A method of, in a human or animal being, performing a capture threshold search using a heart stimulating device that, during normal operation of the device, is set to operate with times VV, AV and/or PV, ER1 and ER2, where VV is a time between a pacing pulse delivered, or inhibited, to a first ventricle and a pacing pulse delivered, or inhibited, during the same heart cycle, to a second ventricle, wherein said time gap VV is $\geq 0$, where AV is a time between a pacing pulse to a first atrium and a subsequent pacing pulse, which may also be inhibited, to said first ventricle, where PV is a time between a sensed event in said first atrium and a subsequent pacing pulse, which may also be inhibited, to said first ventricle, where ER1 is an evoked response detection window for the first ventricle and where ER2 is an evoked response detection window for the second ventricle, said method comprising the steps of:

automatically determining a value V1R2, where V1R2 represents a time between a pacing pulse to the first ventricle and a subsequent event in the second ventricle, during a heart cycle when no pacing pulse is delivered to the second ventricle;

automatically determining $\Delta_{V1R2}$, where $\Delta_{V1R2}$ is a value that takes expected variations in V1R2 into account;

automatically determining a time gap $VV_{cts}$, that is to be used instead of VV during said capture threshold search, with $VV_{cts} \leq V1R2 - ER2 - \Delta_{V1R2}$ but with the additional condition that $VV_{cts}$ shall not be less than 0 even if $V1R2 - ER2 - \Delta_{V1R2}$ is less than 0; and perform a capture threshold search by using $VV_{cts}$, instead of VV.

29. A method according to claim 28, comprising setting $VV_{cts}$ as the smallest of the following values:

VV and $V1R2 - ER2 - \Delta_{V1R2}$, but if $V1R2 - ER2 - \Delta_{V1R2}$ is less than 0, then $VV_{cts}$ is selected to be 0.

30. A method according to claim 28 comprising:

automatically determining a value AR1, where AR1 represents a time between a pacing pulse to the first atrium and a subsequent event in the first ventricle, during a heart cycle when no pacing pulse is delivered to the first ventricle;

automatically determining $\Delta_{AR1}$, where $\Delta_{AR1}$ is a value that takes expected variations in AR1 into account;

automatically determining a time $AV_{cts}$, that is to be used instead of $AV_{cts}$ during said capture threshold search, with $AV_{cts} < AR1 - ER1 - \Delta_{AR1}$ but with the additional condition that AVM shall not be less than a predetermined minimum value for $AV_{cts}$, wherein said minimum value is $\geq 0$, even if $AR1 - ER1 - \Delta_{AR1}$ is less than said minimum value; and perform a capture threshold search by using $AV_{cts}$ instead of AV.

31. A method according to claim 30, comprising:

automatically determining a value AR2, where AR2 is a value which represents the time between a pacing pulse to the first atrium and a subsequent event in the second ventricle, during a heart cycle when no pacing pulse is delivered to the second ventricle;

automatically determining $\Delta_{AR2}$, where $\Delta_{AR2}$ is a value that takes expected variations in AR2 into account;

automatically determining $AV_{cts}$ with $AV_{cts} < AR2 - VV_{cts} - ER2 - \Delta_{AR2}$ but with the additional condition that $AV_{cts}$ shall not be less than a predetermined minimum value for $AV_{cts}$, wherein said minimum value is $\geq 0$, even if $AR2 - VV_{cts} - ER2 - \Delta_{AR2}$ is less than said minimum value; and perform a capture threshold search by using $AV_{cts}$ instead of AV.

32. A method according to claim 31 comprising setting $AV_{cts}$ as the smallest of the following values:

AV, $AR1 - ER1 - \Delta_{AR1}$, and $AR2 - VV_{cts} - ER2 - \Delta_{AR2}$, but with the additional condition that $AV_{cts}$ shall not be less than a predetermined minimum value for $AV_{cts}$, wherein said minimum value is $\geq 0$, even if $AR1 - ER1 - \Delta_{AR1}$ or $AR2 - VV_{cts} - ER2 - \Delta_{AR2}$ is less than said minimum value.

33. A method according to claim 30, comprising employing a minimum value for $AV_{cts}$ that is larger than 0 but less than 90 ms.

34. A method according to claim 33, comprising employing a minimum value for $AV_{cts}$ that is larger than 30 ms but less than 70 ms.

35. A method according to claim 28 comprising:
automatically determining a value PR1, where PR1 represents the time between a sensed event in the first atrium and a subsequent event in the first ventricle, during a heart cycle when no pacing pulse is delivered to the first ventricle;
automatically determining $\Delta_{PR1}$, where $\Delta_{PR1}$ is a value that takes expected variations in PR1 into account;
automatically determining a time $PV_{cts}$, that is to be used instead of PV during said capture threshold search, with $PV_{cts} \leq PR1-ER1-\Delta_{PR1}$ but with the additional condition that $PV_{cts}$ shall not be less than a predetermined minimum value for $PV_{cts}$ wherein said minimum value is $\geq 0$, even if $PR1-ER1-\Delta_{PR1}$ is less than said minimum value; and
perform a capture threshold search by using $PV_{cts}$ instead of PV.

36. A method according to claim 35, comprising:
automatically determining a value PR2, where PR2 is a value which represents a time between a sensed event in the first atrium and a subsequent event in the second ventricle, during a heart cycle when no pacing pulse is delivered to the second ventricle;
automatically determining $\Delta_{PR2}$, where $\Delta_{PR2}$ is a value that takes expected variations in PR2 into account;
automatically determining $PV_{cts}$, with $PV_{cts} \leq PR2-VV_{cts}-ER2-\Delta_{PR2}$ but with the additional condition that $PV_{cts}$ shall not be less than a predetermined minimum value for $PV_{cts}$ wherein said minimum value is $\geq 0$, even if $PR2-VV_{cts}-ER2-\Delta_{PR2}$ is less than said minimum value; and
perform a capture threshold search by using $PV_{cts}$ instead of PV.

37. A method according to claim 36, comprising setting $PV_{cts}$ as the smallest of the following values:

PV, $PR1-ER1-\Delta_{PR1}$, and $PR2-VV_{cts}-ER2-\Delta_{PR2}$, but with the additional condition that $PV_{cts}$, shall not be less than a predetermined minimum value for $PV_{cts}$, wherein said minimum value is $\geq 0$, even if $PR1-ER1-\Delta_{PR1}$ or $PR2-VV_{cts}-ER2-\Delta_{PR2}$ is less than said minimum value.

38. A method according to claim 18, comprising employing a minimum value for $PV_{cts}$ that is larger than 0 but less than 60 ms.

39. A method according to claim 38, comprising employing a minimum value for $PV_{cts}$ that is larger than 10 ms but less than 40 ms.

40. A method according to claim 28 comprising performing the method on a human or animal being suffering from congestive heart failure.

41. A method according to claim 28 comprising performing the method on a human or animal being suffering from a bundle branch block.

* * * * *